(12) United States Patent
Takizawa et al.

(10) Patent No.: US 12,251,121 B2
(45) Date of Patent: Mar. 18, 2025

(54) TREATMENT DEVICE

(71) Applicant: OLYMPUS CORPORATION, Hachioji (JP)

(72) Inventors: Naoki Takizawa, Hirosaki (JP); Motoi Satake, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 810 days.

(21) Appl. No.: 17/190,964

(22) Filed: Mar. 3, 2021

(65) Prior Publication Data

US 2021/0186546 A1 Jun. 24, 2021

Related U.S. Application Data

(63) Continuation of application No. PCT/JP2019/041596, filed on Oct. 24, 2019.

(51) Int. Cl.
*A61B 17/29* (2006.01)
*A61B 17/28* (2006.01)

(52) U.S. Cl.
CPC ............ *A61B 17/29* (2013.01); *A61B 17/282* (2013.01); *A61B 2017/2837* (2013.01)

(58) Field of Classification Search
CPC ........ A61B 17/1285; A61B 2017/2905; A61B 17/29; A61B 17/282; A61B 2017/2837
See application file for complete search history.

(56) References Cited

U.S. PATENT DOCUMENTS

| 2008/0255588 A1* | 10/2008 | Hinman | A61B 17/2909 |
| | | | 606/139 |
| 2013/0123807 A1 | 5/2013 | Wells et al. | |
| 2015/0282826 A1* | 10/2015 | Shoji | A61B 17/29 |
| | | | 606/209 |

(Continued)

FOREIGN PATENT DOCUMENTS

| JP | H01-077703 U | 5/1989 |
| JP | 3370601 B2 | 1/2003 |

(Continued)

OTHER PUBLICATIONS

Espacenet Translation of JP2013085859A (Year: 2013).*

(Continued)

*Primary Examiner* — Katherine H Schwiker
*Assistant Examiner* — Zehra Jaffri
(74) *Attorney, Agent, or Firm* — Oliff PLC

(57) ABSTRACT

A treatment device has an arm member having a plurality of arms to have an open state and a closed state; a wire having a distal end connected to the arm member and the distal end is attachable and detachable to the arm member; a sheath through which the wire is inserted; an operator connected to a proximal end of the sheath; a slider connected to the wire and attached to the operator to be slidable toward a distal end or a proximal end of the operator, wherein the slider makes the plurality of arms to be in the closed state when the slider is disposed in a first range, and the slider makes the plurality of arms to be in the open state when the slider is disposed in a second range; and a slider restriction mechanism provided between the distal end of the operator and the slider.

10 Claims, 12 Drawing Sheets

(56) References Cited

U.S. PATENT DOCUMENTS

2015/0305741 A1* 10/2015 Satake ............... A61B 17/1285
606/142

FOREIGN PATENT DOCUMENTS

| JP | 2013-085859 A | 5/2013 |
|----|---------------|--------|
| WO | 2018-173474 A1 | 9/2018 |

OTHER PUBLICATIONS

Dec. 17, 2019 International Search Report issued in International Application No. PCT/JP2019/041596.
May 10, 2022 Office Action issued in Japanese Patent Application No. 2020-553442.

* cited by examiner

TREATMENT DEVICE

This application is a continuation application of a PCT International Application No. PCT/JP2019/041596, filed on Oct. 24, 2019, whose priority is claimed on a US Provisional Application No. 62/749,877, filed on Oct. 24, 2018. The contents of the PCT International Application and the US provisional Application are incorporated herein by reference.

BACKGROUND

Conventionally, treatment devices (endoscopic treatment devices) are used. The treatment device is connected by a wire, and the treatment device has biopsy forceps protruding from a sheath through the wire is inserted and a treatment mechanism such as grasping forceps, endoscopic clip, and the like. The treatment device reaches the treatment target site through an endoscope channel. The treatment mechanism is configured to operate by moving the wire with respect to the sheath so as to perform the treatment.

The endoscopic treatment device disclosed in Japanese Patent No. 3370601 is configured in consideration of that a substantial length of the sheath changes due to a bending degree when being used and a necessary operation stroke for operating the endoscope treatment device changes. In the endoscopic treatment device disclosed in Japanese Patent No. 3370601, a stopper is provided to restrict a range by which a slider (second finger hook) is able to relatively move with respect to the sheath, wherein the slider is connected to the wire to stroke the wire. According to the endoscopic treatment device disclosed in Japanese Patent No. 3370601, the necessary proper stroke amount is reproduced due to the stopper.

In a case in which the endoscopic clip reaches the treatment target site, when the endoscopic clip is moved in the endoscope channel while the arms are in an open state, distal ends of the arms may come in contact with the endoscope channel and damage the endoscope channel. The arms of the endoscopic clip are biased toward the distal end side. Accordingly, in order to prevent the damage to the endoscope channel, it is necessary for the user to operate the endoscopic clip to reach the treatment target site while pulling the slider to resist the biasing force and thus keep a state in which the arms are accommodated in a pipe provided at the distal end of the sheath.

In the case of making the biopsy forceps and the grasping forceps to reach the treatment target site, when the cup and the grasper are advanced in the endoscope channel in a state of exposing from the pipe provided at the distal end of the sheath, distal ends of the cup and the grasper may come in contact with the endoscope channel and damage the endoscope channel. In order to prevent damage to the endoscope channel, it is necessary for the user to make the biopsy forceps reach the treatment target site while pulling the slider so as to maintain the state in which the cups and the graspers are accommodated in the pipe.

Generally, it is difficult for the user to make the treatment device reach the treatment target site while pulling the slider. In the case of dealing with the endoscopic clip, at the time of making the endoscopic clip reach the treatment target site while pulling the slider, the endoscopic clip may be incorrectly locked if the force for pulling the slider is too strong.

SUMMARY

The present disclosure relates to a treatment device.

One aspect of the present disclosure provides a treatment device including an arm member having a plurality of arms and configured to have an open state and a closed state; a wire having a distal end connected to the arm member, wherein the distal end of the wire is attachable and detachable to the arm member; a sheath through which the wire is inserted; an operator connected to a proximal end of the sheath; a slider connected to the wire and attached to the operator so as to be slidable toward a distal end or a proximal end of the operator, wherein the slider is configured to make the plurality of arms to be in the closed state when the slider is disposed in a first range, and the slider is configured to make the plurality of arms to be in the open state when the slider is disposed in a second range; and a slider restriction mechanism provided between the distal end of the operator and the slider, wherein when the slider is disposed in the first range, the slider restriction mechanism is configured to restrict an operational range of the slider in the first range, and when a user applies a force to move the slider from the first range to the second range, the slider restriction mechanism is configured to transfer a first state in which the operational the slider is restricted in the first range to a second state in which the operational range of the slider includes the first range and the second range.

In other aspects, the treatment device may further include a pipe provided at a distal end of the sheath, wherein the wire is inserted through the sheath, and the pipe is configured to accommodate the arm member, the arm member is configured to take a first position and a second position, the arm member is accommodated in the pipe at the first position, and the arm member is ejected from the distal end of the pipe at the second position, and the arm member is biased from the first position toward the second position.

In other aspects, in a situation when the slider restriction mechanism is in the second state and the arm member is at the second position, the arm member may be moved to the first position by moving the slider to the first range despite of a bending state of the sheath.

In further aspects, the slider restriction mechanism may include a first member and a second member that are movable along a sliding direction of the slider, the first member and the second member may configure a ratchet structure such that the first member and the second member are relatively movable only in a passing-by direction when the first member and the second member are engaged with each other.

In yet further aspects, the slider restriction mechanism may further have a spring having a resistance force against an advancement of the slider, in the first state, a bending degree of the sheath increase such that the sheath extends and the slider moves to the distal end side of the operator, while the slider restriction mechanism is reversibly contracted, and in the second state, the slider restriction mechanism is applied by a force from the distal end of the operator and the slider such that the slider restriction mechanism is irreversibly contracted.

In another aspect, the slider restriction mechanism may include a first member and a second member which are movable along the sliding direction of the slider, and the spring sandwiched by the first member and the second member, the first member and the second member may configure a ratchet structure such that the first member and the second member are relatively movable only in a passing-by direction when the first member and the second member are engaged with each other; the first member and the second member may not engage with each other in the first state, and the first member and the second member may engage with each other in the second state.

In another aspect, the slider restriction mechanism may be configured from a plurality of springs having different yield points, wherein the plurality of springs are continuously provided along the sliding direction of the slider In another aspect, the treatment device may further include an elastic member provided at the pipe, wherein the elastic member has a force to bias the arm member to the second position.

In another aspect, the arm member may be a pair of forceps.

DETAILED DESCRIPTION OF EMBODIMENTS

Hereinafter, an exemplary first embodiment of the present disclosure will be described by referring to FIG. 1 to FIG. 9.

A treatment device 1 according to the present embodiment is a device configured to operate an endoscopic clip EC, for example, to pass through an endoscope channel to reach a treatment target site.

Figure 1:
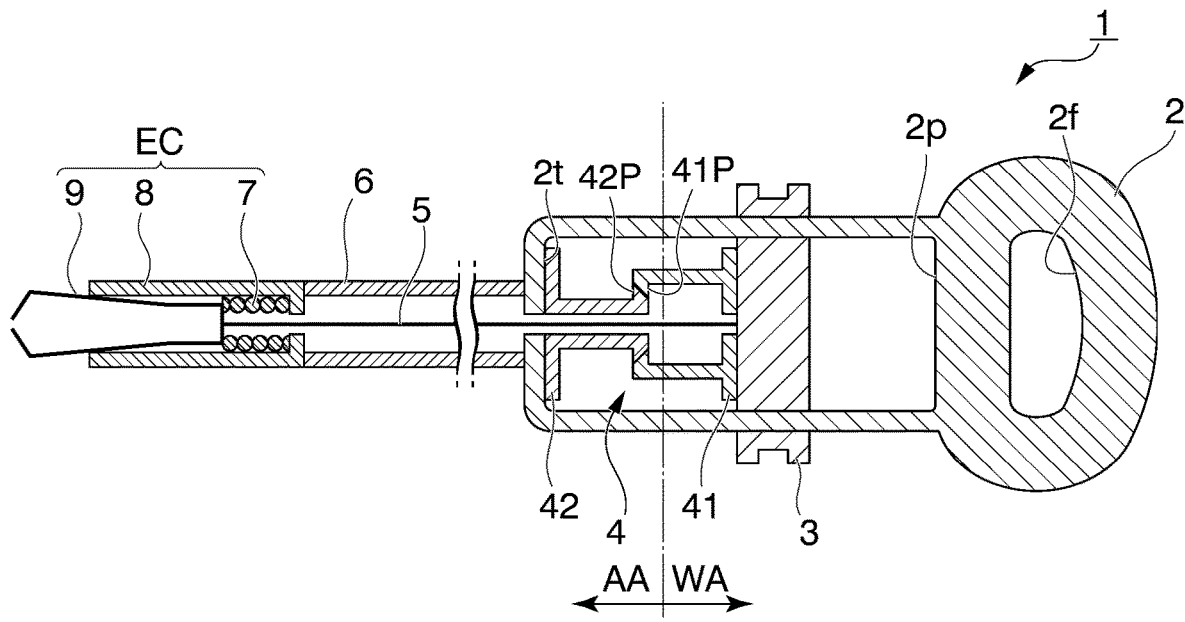
FIG. 1 is a cross-sectional view showing a treatment device according to a first exemplary embodiment and showing a state before the treatment device is used.

FIG. 1 is a cross-sectional view showing the treatment device 1 according to the present embodiment. As shown in FIG. 1, the treatment device 1 has an operation portion (operator) 2, a slider 3, a slider restriction mechanism 4, a wire 5, a sheath 6, and the endoscopic clip EC.

The operation portion 2 is configured for a user to grasp the treatment device 1. A finger hook portion (finger hook) 2f is formed, for example, as a hole having an elliptical shape at the side of the proximal end 2p in the operation portion 2. The user inserts a thumb in the finger hook portion 2f to grasp the treatment device 1.

The slider 3 is configured to move the endoscopic clip EC toward the proximal end side or the distal end side via the wire 5. The slider 3 is attached to the operation portion 2 so as to be slidable between the proximal end 2b and the distal end 2t of the operation portion 2. The user grasps the slider 3 by the forefinger and the middle finger for example and moves the slider 3 between the proximal end 2p and the distal end 2t of the operation portion 2 so as to move the endoscopic clip EC toward the proximal end side and the distal end side.

The slider restriction mechanism 4 is configured to restrict the movement of the slider 3 by resisting the bias toward the distal end side where the endoscopic clip is provided. The slider restriction mechanism 4 is provided between the distal end 2t and the proximal end 2p of the operation portion 2, and the wire 5 is inserted through the slider restriction mechanism 4.

The slider restriction mechanism 4 has a grasping portion (first member) 41 and a grasped portion (second member) 42. Each of the grasping portion 41 and the grasped portion 42 has a hollow portion formed along an axial direction, and the wire 5 is inserted through the hollow portion. Each of the grasping portion 41 and the grasped portion 42 has an asymmetrical shape with respect to the axis.

The grasping portion 41 and the grasped portion 42 configure a ratchet mechanism. In a case in which the grasping portion 41 and the grasped portion 42 come in contact with each other and move in the passing-by direction (opposite direction) with respect to each other since the slider restriction mechanism 4 is contracted, it is possible that a protrusion 41P of the grasping portion 41 and a protrusion 42P of the grasped portion 42 get over each other and pass by each other. When the protrusion 41P and the protrusion 42P get over each other, since the protrusion 41P and the protrusion 42P engage with each other, the movement in the direction in which the protrusion 41P and the protrusion 42P separate from each other is prevented. According to the present embodiment, one protrusion 42P of the grasped portion 42 is provided along the axial direction, a plurality of the protrusions 42P may be provided.

The wire 5 is configured to move the endoscopic clip EC toward the distal end side in association with the stroke by the slider 3. The wire 5 is configured to have a distal end attachably and detachably connected to the endoscopic clip EC and a proximal end connected to the slider 3.

The sheath 6 is configured to assist the operation of the endoscopic clip EC. The sheath 6 is configured to have a proximal end connected to the distal end 2t of the operation portion 2 and a distal end, wherein the wire 5 is inserted through the sheath 6, and the endoscopic clip EC is exposed from the distal end of the sheath 6.

The endoscopic clip EC is configured to ligate openings, the blood vessels and the like formed in the human body. The endoscopic clip EC has an elastic member 7, a pipe 8, and an arm member (arm) 9.

Figure 2:
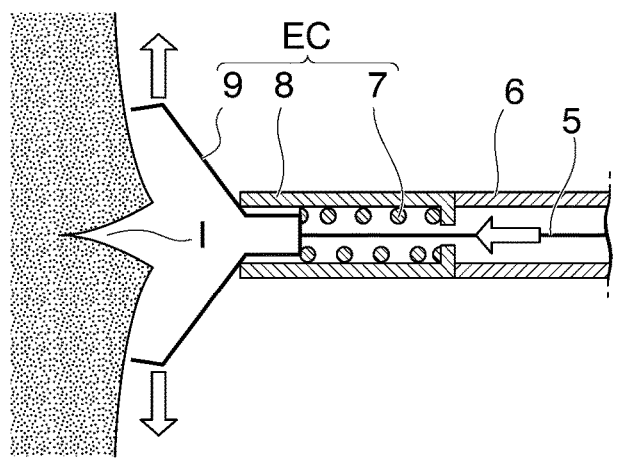
FIG. 2 is an enlarged cross-sectional view showing a circumference of an endoscopic clip according to the first embodiment and showing an open state of arm members.

As shown in FIG. 1 and FIG. 2, the arm member 9 is configured to transfer between a first position where the arm member 9 is pressed by the pipe 8 to be in a closed state and a second position where the arm member 9 is released from the pipe 8 to be in an open state due to the biasing force of the arm member 9 itself.

The elastic member 7 is configured to definitely move the arm member 9 toward the distal end side and make the arm member 9 to transfer to the second position in the case where the wire 5 moves toward the distal end side. The elastic member 7 is configured to bias the arm member 9 toward the second position when the arm member is positioned at the first position due to the restoring force. The elastic member 7 is configured to move the arm member 9 toward the distal end side by the restoring force when the wire 5 moves toward the distal end side, and the elastic member 7 releases the arm member 9 from the biased state when the arm member 9 transfers to the second position.

The slider 3 moves the arm member 9 into an operation range AA set in the second position by advancing the arm member 9 from a standby range WA set in the first position.

The protrusion 41P of the grasping portion 41 and the protrusion 42P of the grasped portion 42 cannot get over each other due to the compression force from the elastic member 7 via the slider 3.

Operation of the treatment device 1 will be described. FIG. 1 is a view showing the state before the usage of the treatment device 1. In the state before the usage of the treatment device 1, the sheath 6 is in a straight state. The biasing force by the elastic member 7 applies to the arm member 9. The force toward the proximal end side by the slider restriction mechanism 4 via the wire 5 and the slider 3 applies to the arm member 9. The biasing force by the elastic member 7 and the force by the slider restriction mechanism 4 are balanced with each other such that the arm member 9 is stationary at the first position. The slider restriction mechanism 4 restricts the operation of the slider 3 in the standby range WA (first range, first state).

The user pushes the operation portion 2 without applying any force to the slider 3 to make the treatment device 1 to pass through the endoscope channel (not shown) to reach the treatment target site. At this time, the first state is maintained.

As shown in FIG. 2, when the user makes the treatment device 1 reach the treatment target site and turns the endoscopic clip EC toward the opening I, the user strokes and advances the slider 3 toward the distal end side to move the arm member 9 to the second position.

Figure 3:
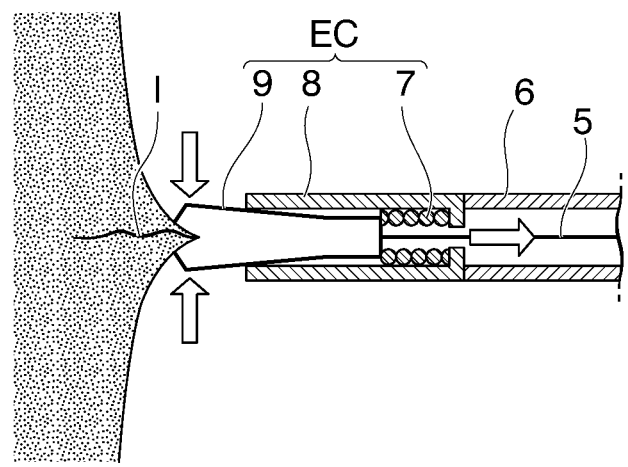
FIG. 3 is a view showing the arms operated from the state shown in FIG. 2 to a closed state.

As shown in FIG. 3, the user pulls back the slider 3 and moves the arm member 9 to the first position so as to grasp the edge of the opening I by the arm member 9 and close the opening I.

Figure 4:
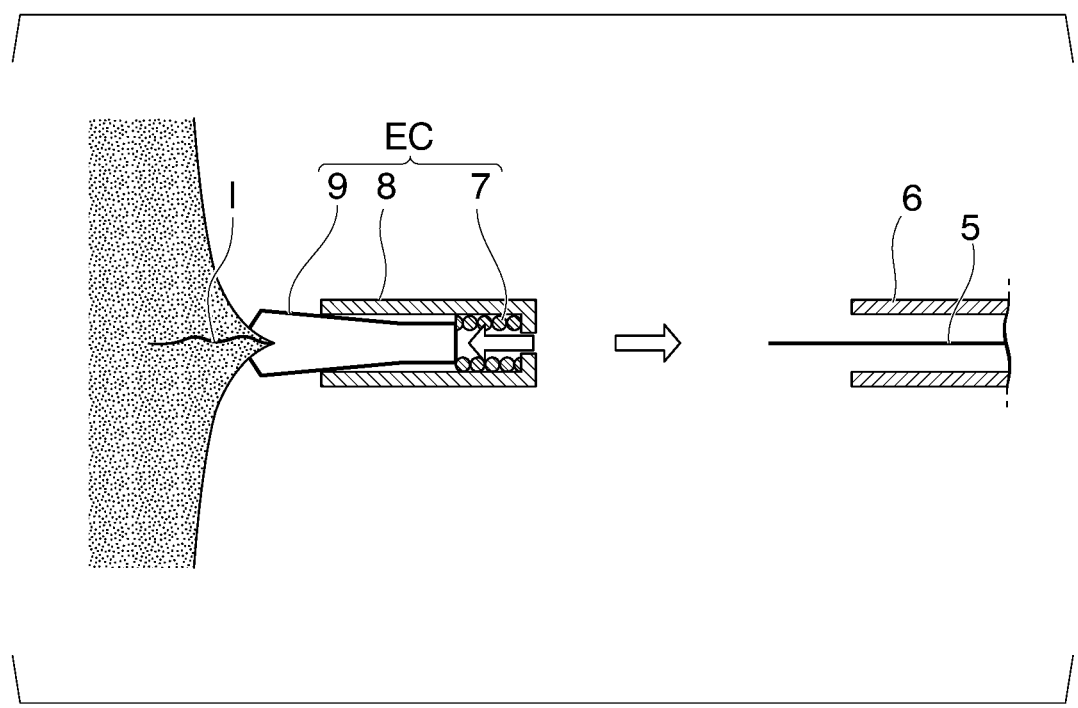
FIG. 4 is a view showing the endoscopic clip separated from the state shown in FIG. 3.

As shown in FIG. 4, the user pulls the slider 3 by a force exceeding a certain amount such that the arm member 9 is separated from the wire 5. The arm member 9 separated from the wire 5 is pressed by the pipe 8 to maintain the closed state so as to be indwelled at the treatment target site while closing the opening I.

Figure 5:
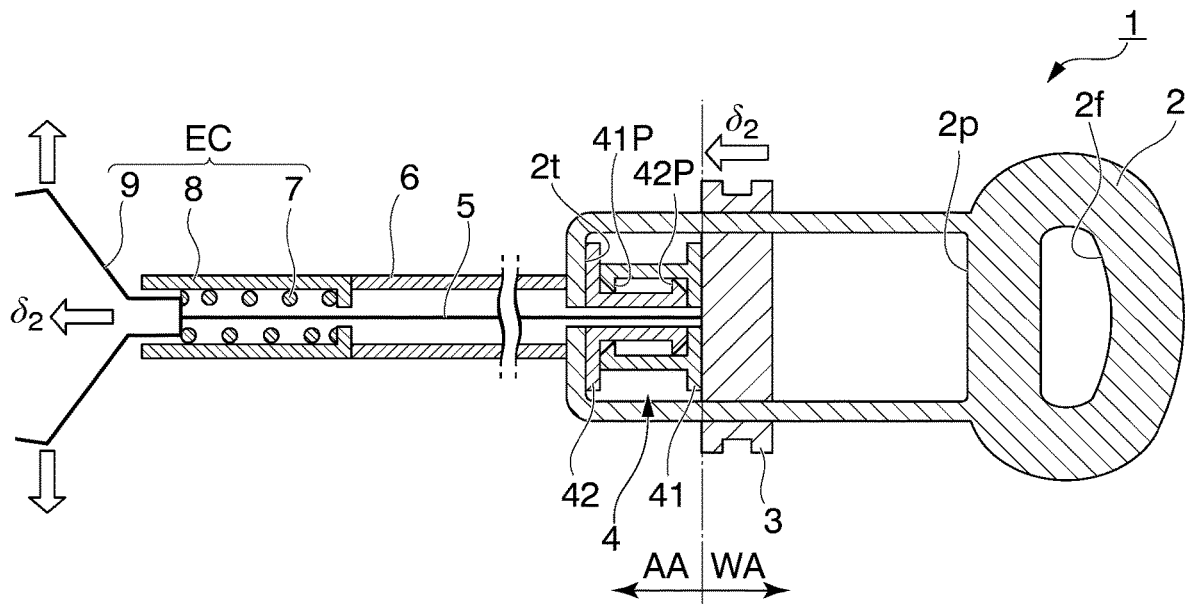
FIG. 5 is a cross-sectional view of the treatment device shown in FIG. 1 when a sheath is in a straight state and the arm members are in the open state.

As shown in FIG. 5, in the treatment device 1, the arm member 9 is operated to the second position by applying the force to make the protrusion 41P of the grasping portion 41 to get over the protrusion 42P of the grasped portion 42 and advance the slider 3. The slider restriction mechanism 4 is contracted such that the operation range of the slider 3 is set to the standby range WA and the operation range AA (second range, second state).

Figure 6:
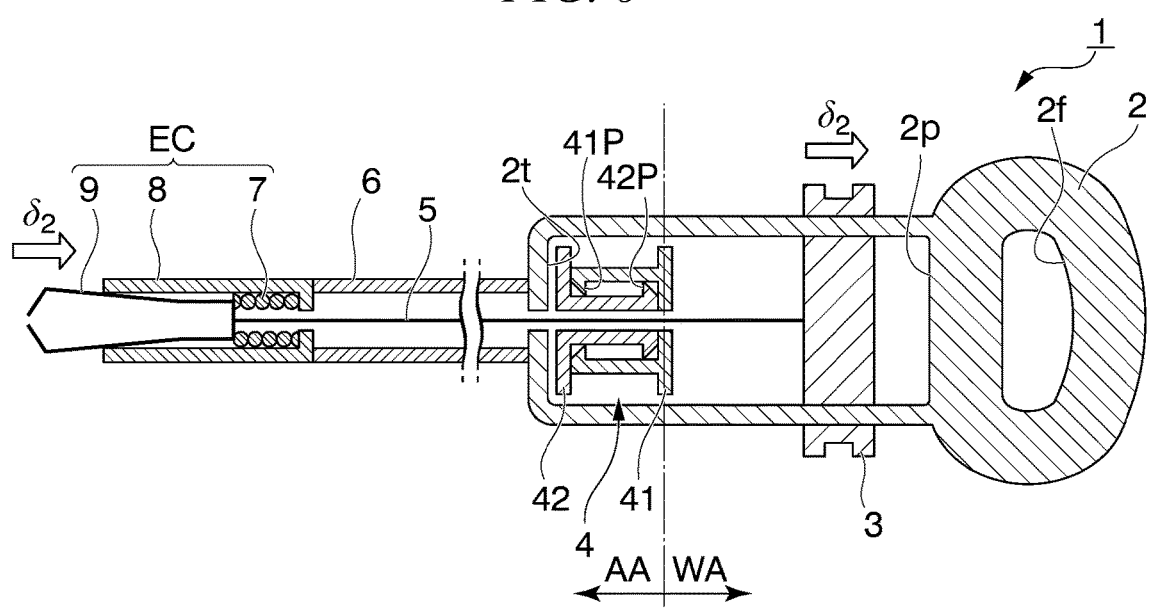
FIG. 6 is a view showing an operation of moving a slider toward a proximal end side of an operation portion.

As shown in FIG. 6, when the slider restriction mechanism 4 is in the second state and the user pulls back the slider 3 to the standby range WA, the arm member 9 returns to the first position again. When the user releases the force applied to the slider 3, due to the storing force of the elastic member 7, the slider 3 moves to the operation range AA and the arm member 9 moves to the second position again. Accordingly, even if a failure occurs during the operation of grasping the edge of the opening I to close the opening I, it is possible to perform the grasping operation again.

According to the treatment device 1 according to the present embodiment, the bias applied to the arm member 9 toward the distal end side in the standby range is suppressed by the slider restriction mechanism 4 via the wire 5 and the slider 3. Accordingly, at the time of making the treatment device 1 reach the treatment target site while accommodating the arm member 9 in the pipe 8, it is not necessary for the user to pull the slider 3.

Next, an exemplary second embodiment of the present disclosure will be described by referring to FIG. 7 to FIG. 14.

A treatment device 1A according to the present embodiment, similar to the treatment device 1, is a device configured to make the endoscopic clip EC, for example, reach a treatment target site by passing through the endoscope channel and operate the endoscopic clip EC. The treatment device 1A is configured to have a slider restriction mechanism 4A instead of the slider restriction mechanism 4 in the treatment device 1. Accordingly, only the matters influenced by having the slider restriction mechanism 4A instead of the slider restriction mechanism 4 will be described.

Figure 7:
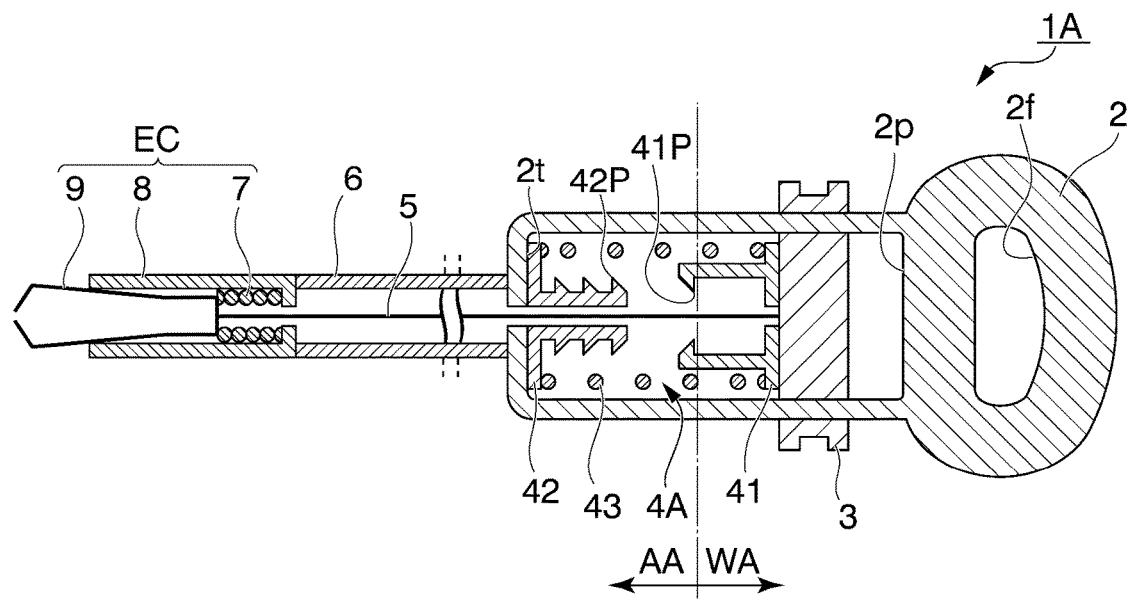
FIG. 7 is a cross-sectional view showing a treatment device according to a second exemplary embodiment and showing a state before the treatment device is used.

As shown in FIG. 7, the slider restriction mechanism 4A has the grasping portion (first member) 41, the grasped portion (second member) 42, and a spring 43. The spring 43 is sandwiched by the grasping portion 41 and the grasped portion 42. Each of the grasping portion 41 and the grasped portion 42 has a hollow portion formed along an axial direction, and the wire 5 is inserted through the hollow portion. Each of the grasping portion 41 and the grasped portion 42 has an asymmetrical shape with respect to the axis. The slider restriction mechanism 4A is contracted by applying a compression force in the axial direction which is larger than the restoring force of the spring 43. Accordingly to the present embodiment, three protrusions 42P of the grasped portion 42 are provided along the axial direction, however, it only has to provide at least one protrusion 42P.

Operations of the treatment device 1A will be described. FIG. 7 is a view showing the state before the usage of the treatment device 1A. In the state before the usage of the treatment device 1A, the biasing force applied to the arm member 9 by the elastic member 7 and the force toward the proximal end side by the spring 43 are balanced with each other such that the arm member 9 is stationary at the first position. The slider 3 receives a resistance force by the spring 43 against advancement.

Figure 8:
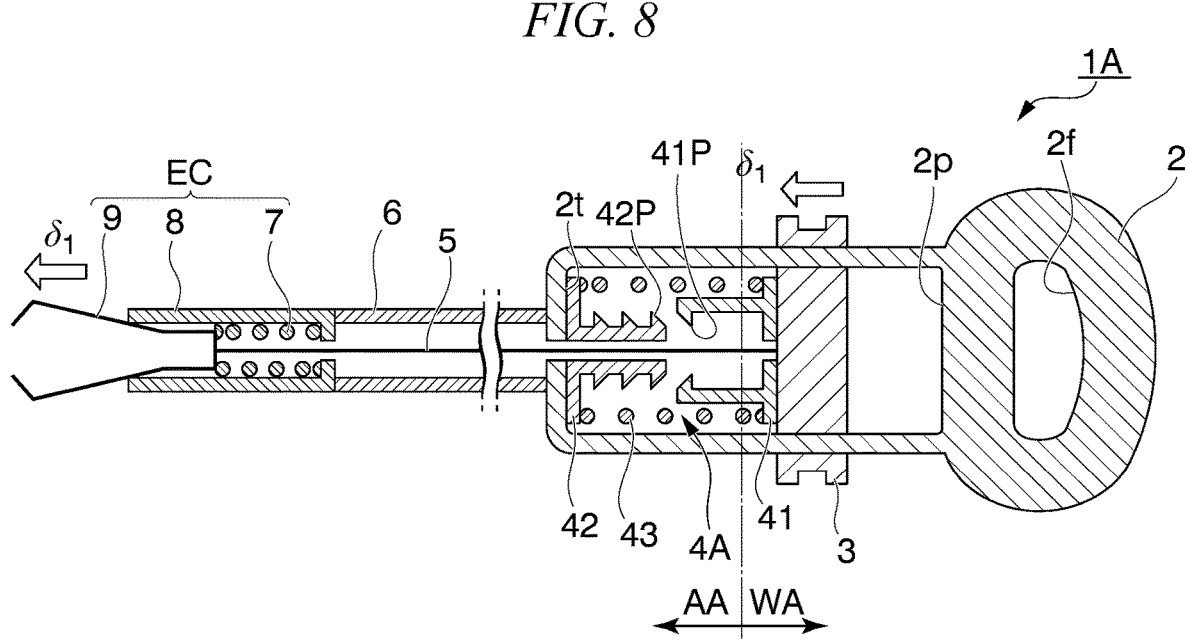
FIG. 8 is a view showing a state when a slider is moved toward a distal end side from the state shown in FIG. 7.

FIG. 8 is a view showing a state in which the user strokes the slider 3 toward the distal end side by a stroke amount in a range to maintain the arm member 9 at the first position when the sheath 6 is in the straight state. When the arm member 9 is in the range, the grasping portion 41 and the grasped portion 42 do not engage with each other. When the user releases the force applied to the slider 3, the restoring force by the spring 43 of the slider restriction mechanism 4A surpasses the restoring force of the elastic member 7 such that the slider restriction mechanism 4A pushes back the slider 3. The slider restriction mechanism 4A restricts the operation of the slider 3 in the standby region WA (first state).

Figure 9:
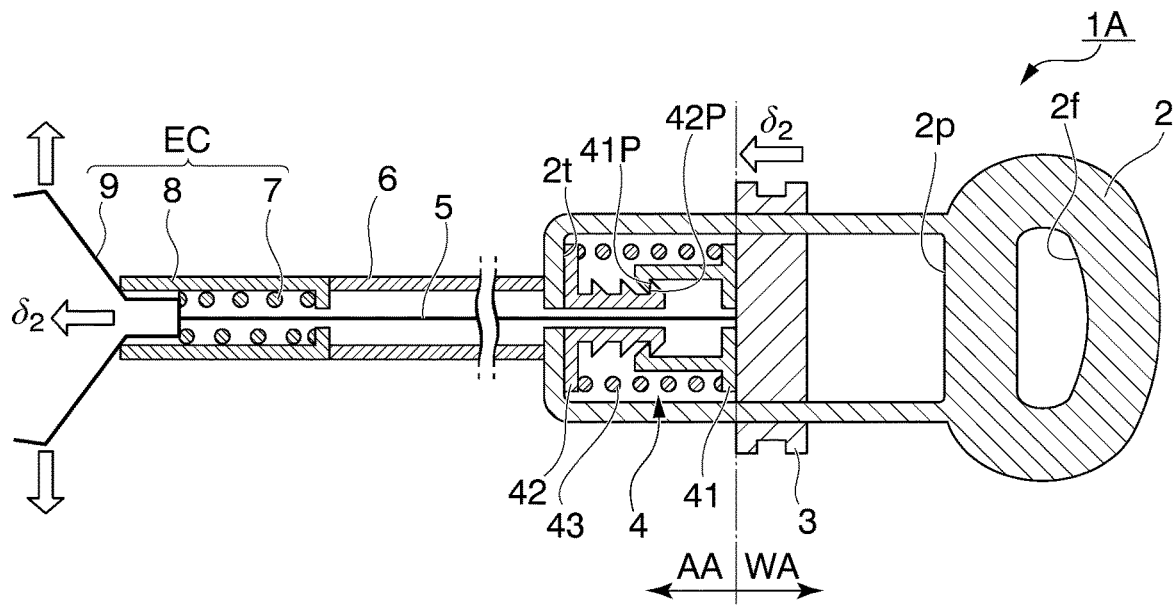
FIG. 9 is a view showing a state when the slider is moved in an operational range.

As shown in FIG. 9, in the treatment device 1A, the sheath 6 is in the straight state, the arm member 9 transfers to the second position by applying a force resisting the restoring force of the spring 43 so as to make the protrusion 41P of the grasping portion 41 to get over the most proximal protrusion 42P of the grasped portion 42 and advance the slider 3. The slider restriction mechanism 4A is contracted such that the operation range of the slider 3 is set to the standby range WA and the operational range AA (second state).

The contraction of the slider restriction mechanism 4A is an irreversible contraction to cancel the restoration of the spring 43 due to the engagement of the protrusion 41P and the protrusion 42P.

In the state, the slider restriction mechanism 4A does not push back the slider 3 toward the proximal end side by the restoring force of the spring 43. Accordingly, even if the user releases the force applied to the slider 3, the slider 3 is maintained in the operational range AA due to the restoring force of the elastic member 7. The slider restriction mechanism 4A is contracted such that the operation range of the slider 3 is set to the standby range WA and the operational range AA (second state).

Figure 10:
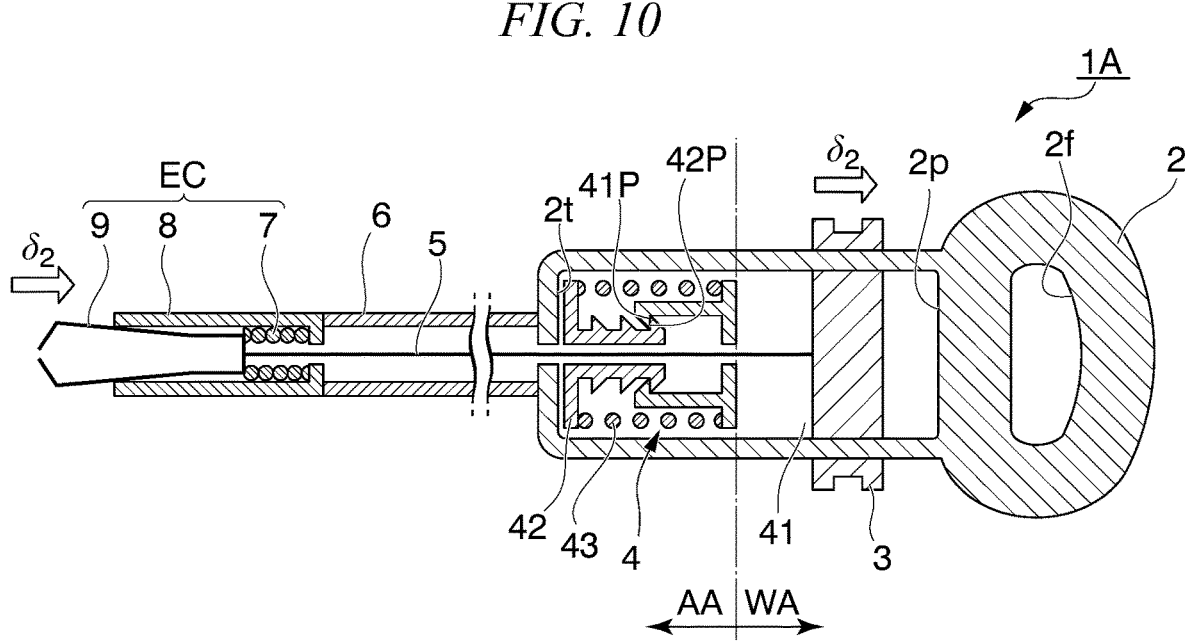
FIG. 10 is a view showing a state when the slider is moved in a standby range.

As shown in FIG. 10, when the slider restriction mechanism 4A is in the second state and the user pulls the slider 3 back to the standby range WA, the arm member 9 takes the first position again. When the user releases the force applied to the slider 3, the slider 3 moves to the operational range AA due to the restoring force of the elastic member 7 such that the arm member 9 takes the second position again. Accordingly, even if a failure occurs during the operation of grasping the edge of the opening I to close the opening I, it is possible to perform the grasping operation again.

Figure 11:
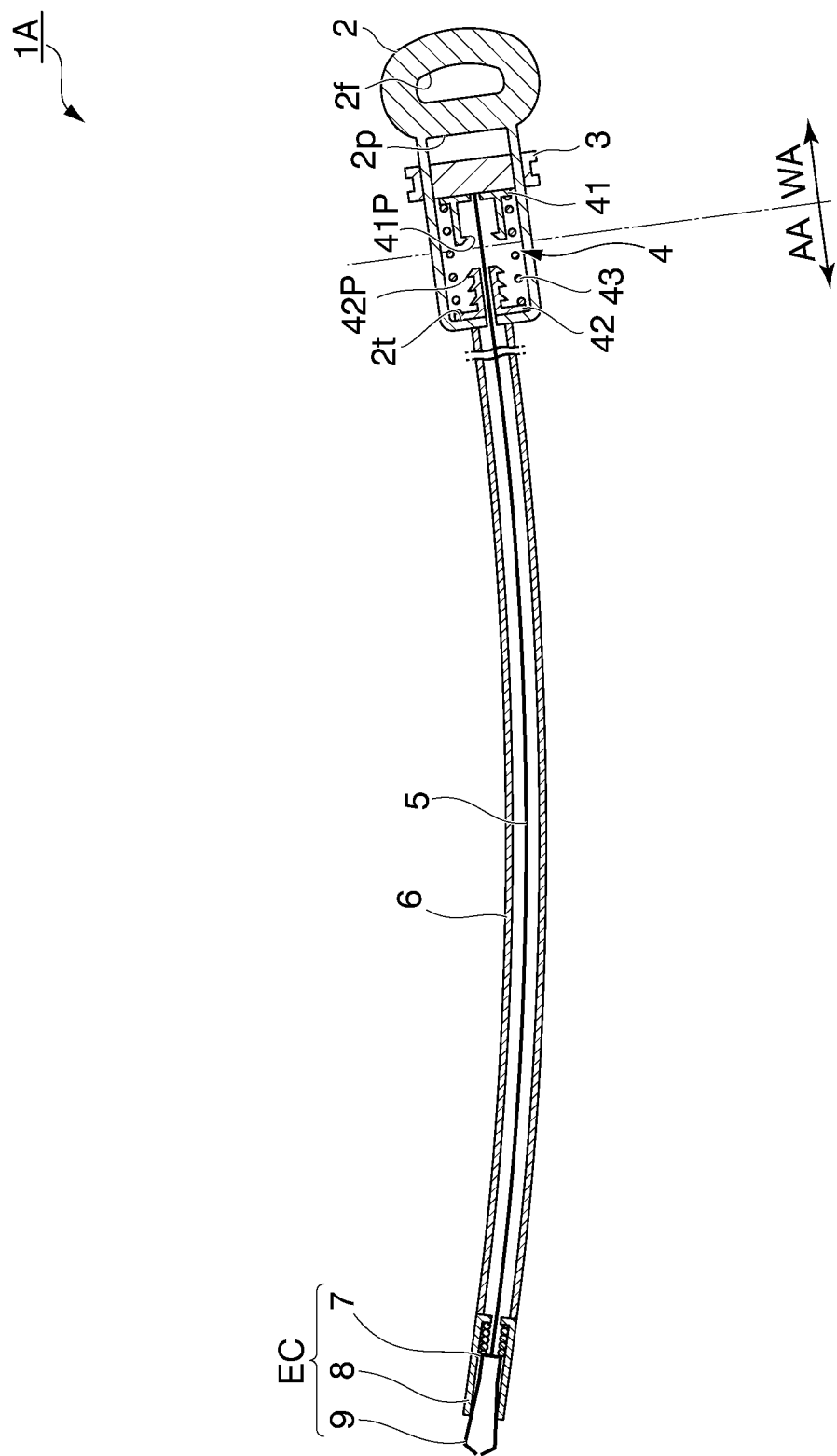
FIG. 11 is a cross-sectional view showing the treatment device shown in FIG. 1 and showing a standby range when the sheath is in a bending state.

As shown in FIG. 11, the treatment device 1A is configured to substantially extend the sheath 6 when the sheath 6 is in a bending state. The sheath 6 applies a force toward the distal end side to the endoscopic clip EC due to the substantial extension. Accordingly, the slider restriction mechanism 4A is compressed to be contracted via the wire 5 and the slider 3 so as to advance the slider 3 toward the distal end side. Compared with the situation when the sheath 6 is in the straight state, the standby range WA is expanded at the side of the distal end 2t of the operation portion 2. The contraction of the slider restriction mechanism 4A is a reversible contraction due to the elastic deformation of the spring 43.

FIG. 11 is a view showing a state in which the arm member 9 is in the range to maintain the first position when the sheath 6 is in the bending state. The arm member 9 is in the range such that the grasping portion 41 and the grasped portion 42 do not engage with each other. In the range, the user strokes the slider 3 toward the distal end side and then releases the force applied to the slider 3, the restoring force by the spring 43 of the slider restriction mechanism 4A surpasses the restoring force of the elastic member 7 such that the slider restriction mechanism 4A pushes back the slider 3. The slider restriction mechanism 4A restricts the operation of the slider 3 in the standby region WA (first state).

Figure 12:
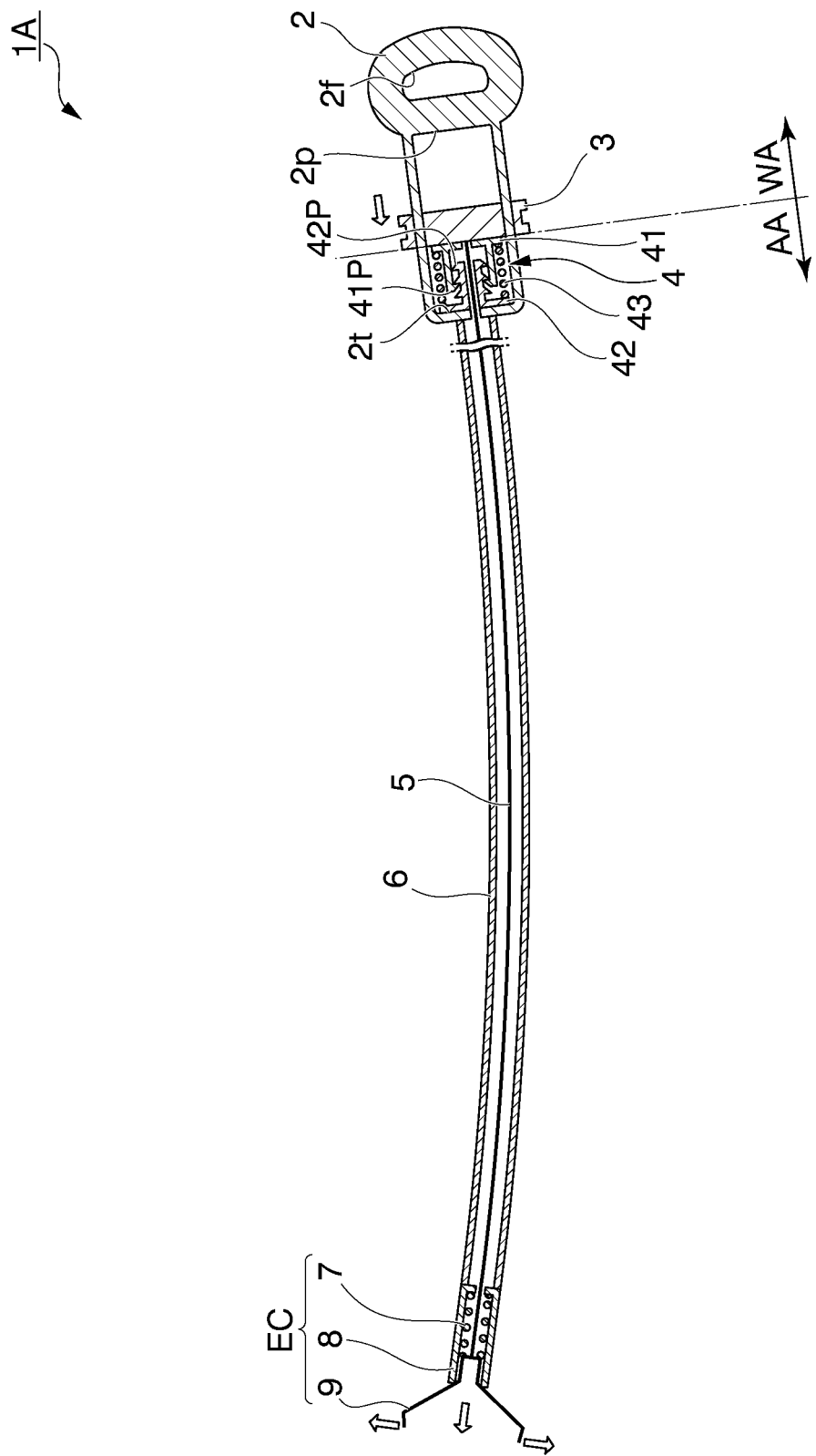
FIG. 12 is a cross-sectional view showing the treatment device shown in FIG. 1 and showing an operational range when the sheath is in the bending state.

As shown in FIG. 12, when the sheath 6 is in the bent state, the arm member 9 transfers to the second position by applying a force resisting the restoring force of the spring 43 so as to make the protrusion 41P of the grasping portion 41 to get over the most proximal protrusion 42P of the grasped portion 42 and advance the slider 3. The slider restriction mechanism 4A is contracted such that the operation range of the slider 3 is set to the standby range WA and the operational range AA (second state).

The contraction of the slider restriction mechanism 4A is an irreversible contraction to cancel the restoration of the spring 43 due to the engagement of the protrusion 41P and the protrusion 42P.

In the state, the slider restriction mechanism 4A does not push back the slider 3 toward the proximal end side by the restoring force of the spring 43. Accordingly, even if the user releases the force applied to the slider 3, the slider 3 is maintained in the operational range AA due to the restoring force of the elastic member 7. The slider restriction mechanism 4A is contracted such that the operation range of the slider 3 is set to the standby range WA and the operational range AA (second state).

When the slider restriction mechanism 4A is in the second state and the user pulls the slider 3 back to the standby range WA, the arm member 9 takes the first position again. When the user releases the force applied to the slider 3, the slider 3 moves to the operational range AA due to the restoring force of the elastic member 7 such that the arm member 9 takes the second position again. Accordingly, even if a failure occurs during the operation of grasping the edge of the opening I to close the opening I, it is possible to perform the grasping operation again.

Figure 13:
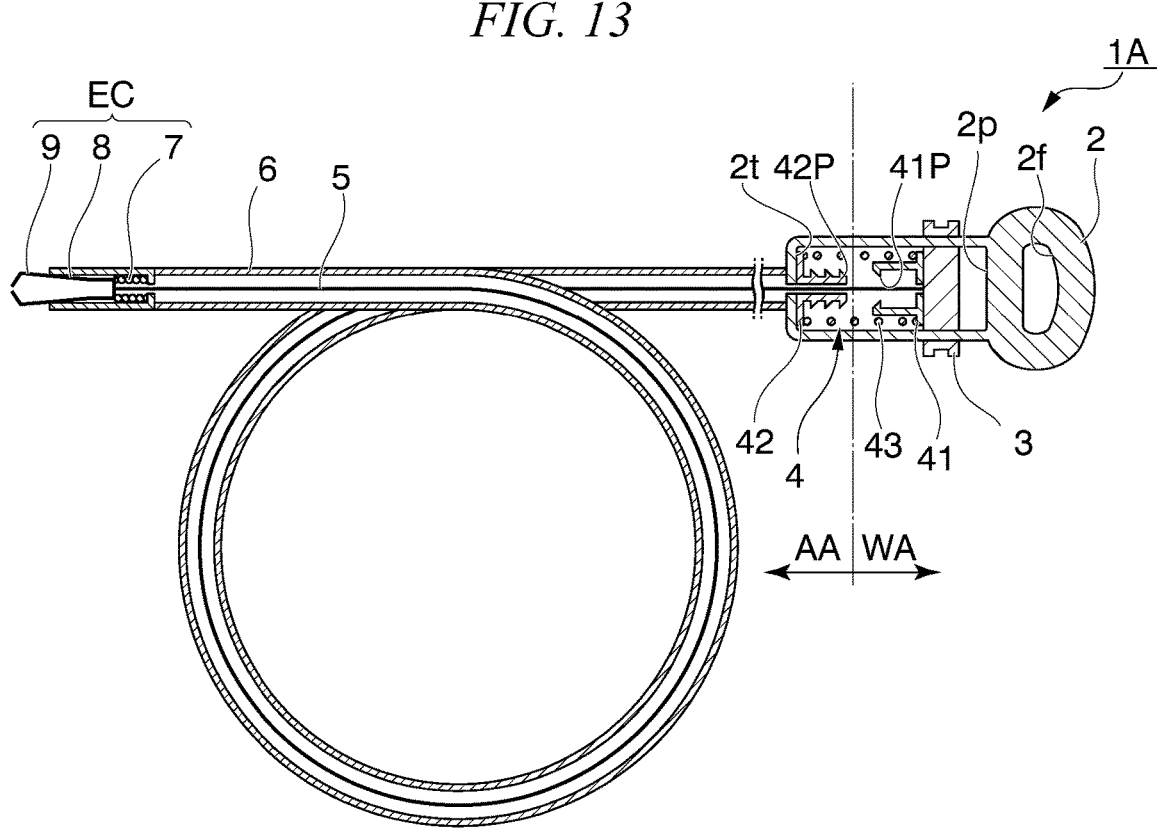
FIG. 13 is a cross-sectional view showing the treatment device shown in FIG. 1 and showing a standby range when the sheath is in a once-wrapped state.

As shown in FIG. 13, the treatment device 1A is configured to substantially extend the sheath 6 when the sheath 6 is in the once-wrapped state. The sheath 6 applies a force toward the distal end side to the endoscopic clip EC due to the substantial extension. Accordingly, the slider restriction mechanism 4A is compressed to be contracted via the wire 5 and the slider 3 so as to advance the slider 3 toward the distal end side. Compared with the situation when the sheath 6 is in the bent state, the standby range WA is expanded at the side of the distal end 2t of the operation portion 2. The contraction of the slider restriction mechanism 4A is a reversible contraction due to the elastic deformation of the spring 43.

FIG. 13 is a view showing a state in which the arm member 9 is in the range to maintain the first position when the sheath 6 is in the once-wrapped state. The arm member 9 is in the range such that the grasping portion 41 and the grasped portion 42 do not engage with each other. In the range, the user strokes the slider 3 toward the distal end side and then releases the force applied to the slider 3, the restoring force by the spring 43 of the slider restriction mechanism 4A surpasses the restoring force of the elastic member 7 such that the slider restriction mechanism 4A pushes back the slider 3. The slider restriction mechanism 4A restricts the operation of the slider 3 in the standby region WA (first state).

Figure 14:
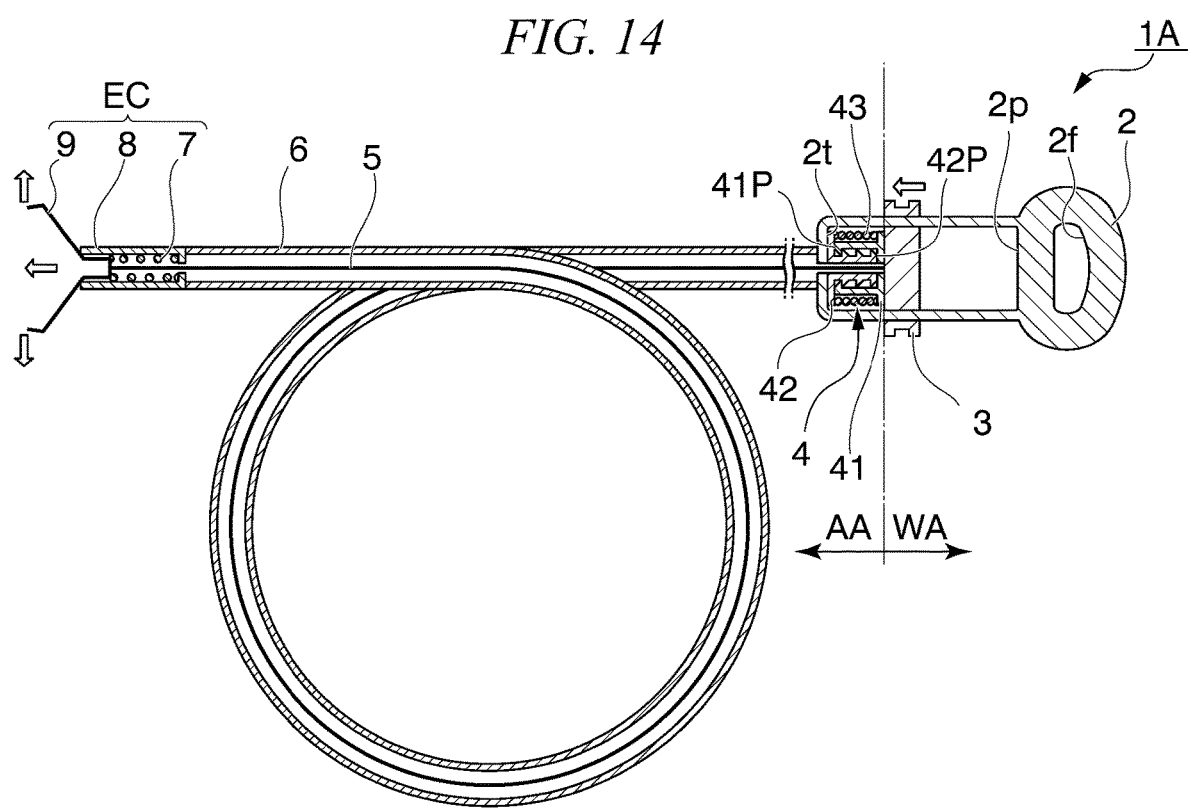
FIG. 14 is a cross-sectional view showing the treatment device shown in FIG. 1 and showing an operational range when the sheath is in the once-wrapped state.

As shown in FIG. 14, when the sheath 6 is in the once-wrapped state, the arm member 9 transfers to the second position by applying a force resisting the restoring force of the spring 43 so as to make the protrusion 41P of the grasping portion 41 to get over the most proximal protrusion 42P of the grasped portion 42 and advance the slider 3. The slider restriction mechanism 4A is contracted such that the operation range of the slider 3 is set to the standby range WA and the operational range AA (second state).

The contraction of the slider restriction mechanism 4A is an irreversible contraction to cancel the restoration of the spring 43 due to the engagement of the protrusion 41P and the protrusion 42P.

In the state, the slider restriction mechanism 4A does not push back the slider 3 toward the proximal end side by the restoring force of the spring 43. Accordingly, even if the user releases the force applied to the slider 3, the slider 3 is maintained in the operational range AA due to the restoring force of the elastic member 7. The slider restriction mechanism 4A is contracted such that the operation range of the slider 3 is set to the standby range WA and the operational range AA (second state).

When the slider restriction mechanism 4A is in the second state and the user pulls the slider 3 back to the standby range WA, the arm member 9 takes the first position again. When the user releases the force applied to the slider 3, the slider 3 moves to the operational range AA due to the restoring force of the elastic member 7 such that the arm member 9 takes the second position again. Accordingly, even if a failure occurs during the operation of grasping the edge of the opening I to close the opening I, it is possible to perform the grasping operation again.

According to the treatment device 1A according to the present embodiment, despite of the bending state of the sheath 6, the bias toward the distal end side applied to the arm member 9 in the standby range WA is suppressed by the slider restriction mechanism 4A via the wire 5 and the slider 3. Accordingly, despite of the bending state of the sheath 6, at the time of making the treatment device 1A reach the treatment target site while accommodating the arm member 9 in the pipe 8, it is not necessary for the user to pull the slider 3.

Furthermore, the spring 43 has the resistance force against the advancement of the slider 3 such that even if the user does not pull the slider 3, the arm member 9 will not project out suddenly. For example, the arm member will not project out to damage the mucous membrane at the treatment target site.

Next, an exemplary third embodiment of the present disclosure will be described by referring to FIG. 15 to FIG. 20.

A treatment device 1B according to the present embodiment, similar to the treatment device 1, is a device configured to make the endoscopic clip EC, for example, reach a treatment target site by passing through the endoscope channel and operate the endoscopic clip EC. The treatment device 1B is configured to have a slider restriction mechanism 10 instead of the slider restriction mechanism 4A in the treatment device 1A.

Figure 15:
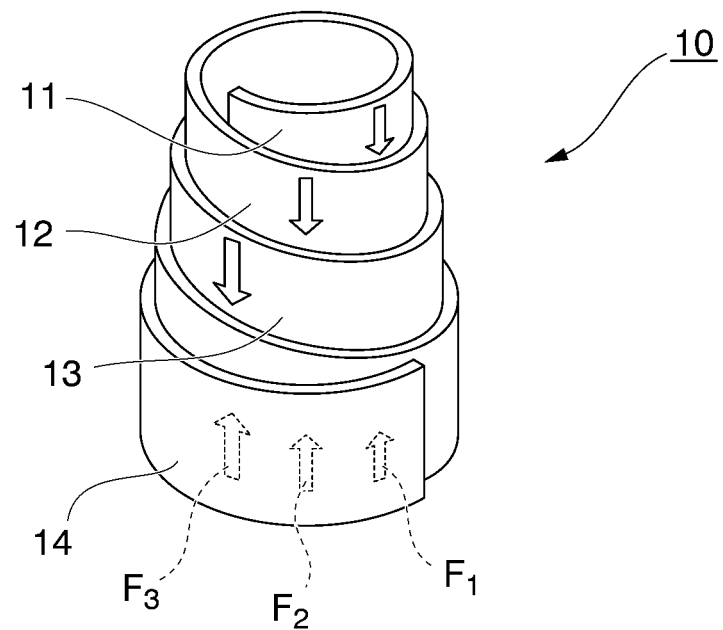
FIG. 15 is a perspective view showing a slider restriction mechanism of a treatment device according to a third exemplary embodiment.
Figure 16:
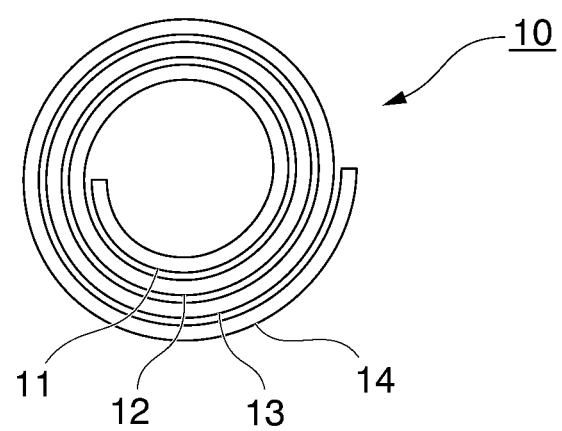
FIG. 16 is a planar view showing the slider restriction mechanism in FIG. 15.

FIG. 15 is a perspective view of the slider restriction mechanism 10 of the treatment device 1B. FIG. 16 is a planar view of the slider restriction mechanism 10. As shown in FIGS. 15 and 16, the slider restriction mechanism 10 is a spiral spring, wherein the coils of the spiral spring is separated from the axial direction from the inside coil to the outside coil.

The slider restriction mechanism 10 is designed to have a strength distribution that as the compression force applied long the axial direction increases, the coils yield in a sequence from the inside coil to the outside coil. A yield point F2 of a second coil 12 is larger than the yield point F1 of the most inside coil 11. The yield point F3 of a third coil 13 is larger than the yield point F2 of the second coil 12.

According to the present embodiment, with regard to the slider restriction mechanism 10, a number of the wound coils of the spiral spring is determined to be three windings along the axial direction excluding the end coil 14, however, only one or more windings has to be formed.

Operations of the treatment device 1B will be described. The only one difference between the operations of the treatment device 1B and that of the treatment device 1A is that manners of the dimension reduction in the axial direction between the slider restriction mechanism 10 and the slider restriction mechanism 4A are different from each other. Accordingly, the manner of the dimension reduction in the axial direction of the slider restriction mechanism 10 will be described.

Figure 17:
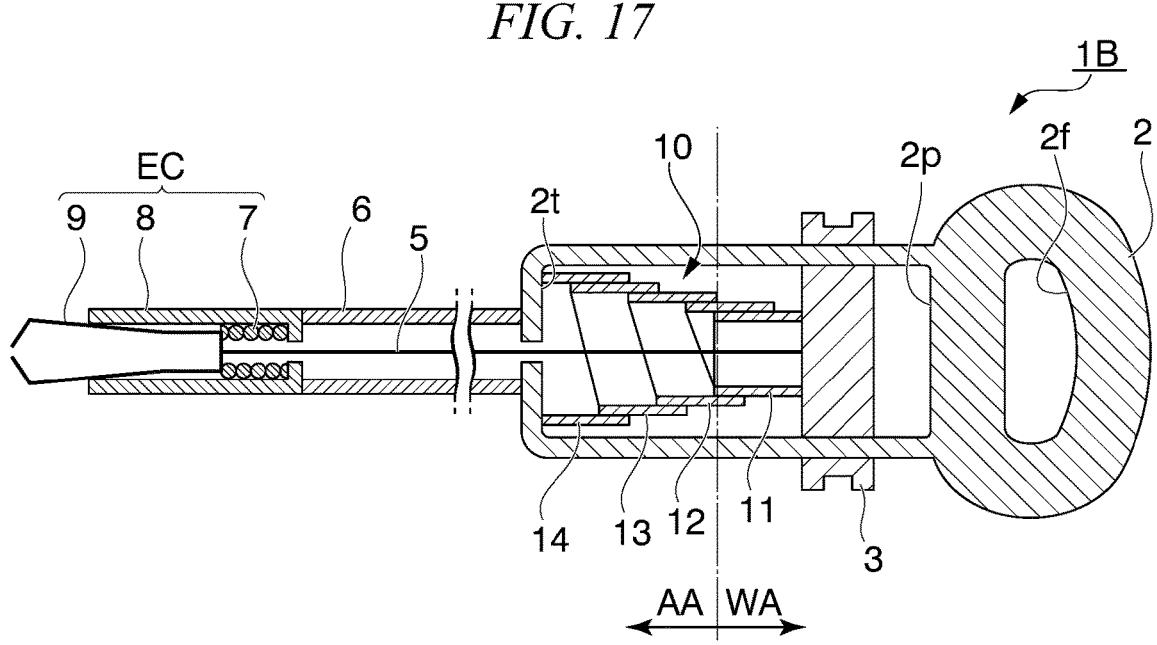
FIG. 17 is a cross-sectional view showing the treatment device according to the third embodiment and showing a state before the treatment device is used.

FIG. 17 is a view showing the state before the usage of the treatment device 1B. In the state before the usage of the treatment device 1B, the force toward the proximal end side by the slider restriction mechanism 10 and via the wire 5 and the slider 3 is applied to the arm member 9. The biasing force by the elastic member 7 and the force by the slider restriction mechanism 10 are balanced with each other such that the arm member 9 is in the stationary state at the first position.

The treatment device 1B is configured to restrict the operations of the slider 3 in the standby region WA due to the elasticity provided by the slider restriction mechanism 10 (first state).

Figure 18:
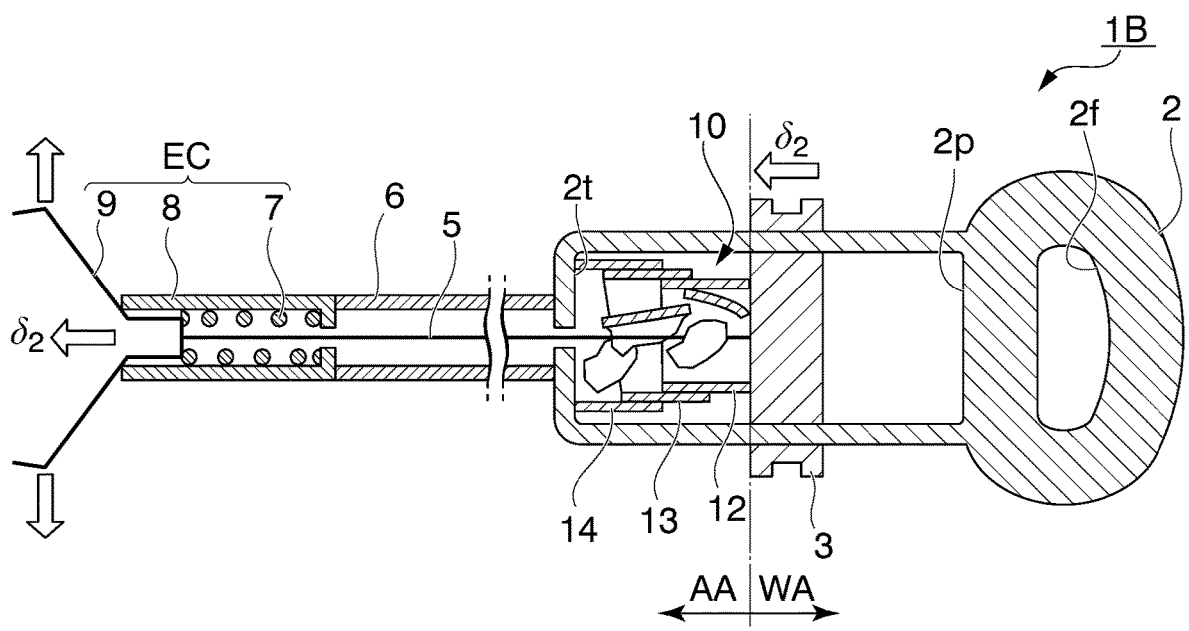
FIG. 18 is a cross-sectional view showing the treatment device in FIG. 17 and showing an operational range when the sheath is in a straight state.

As shown in FIG. 18, the treatment device 1B is configured that the compression force F1 applies to the coil 11 so as to cause the coil 11 to yield at the stroke amount that the arm member 9 is at the second position when the sheath 6 is in the straight state. Since the coil 11 yields to the compression force F1, the dimension in the axial direction of the slider restriction mechanism 10 reduces. The slider restriction mechanism 10 is contracted such that the operation range of the slider 3 becomes to the standby range WA and the operational range AA (second state).

Figure 19:
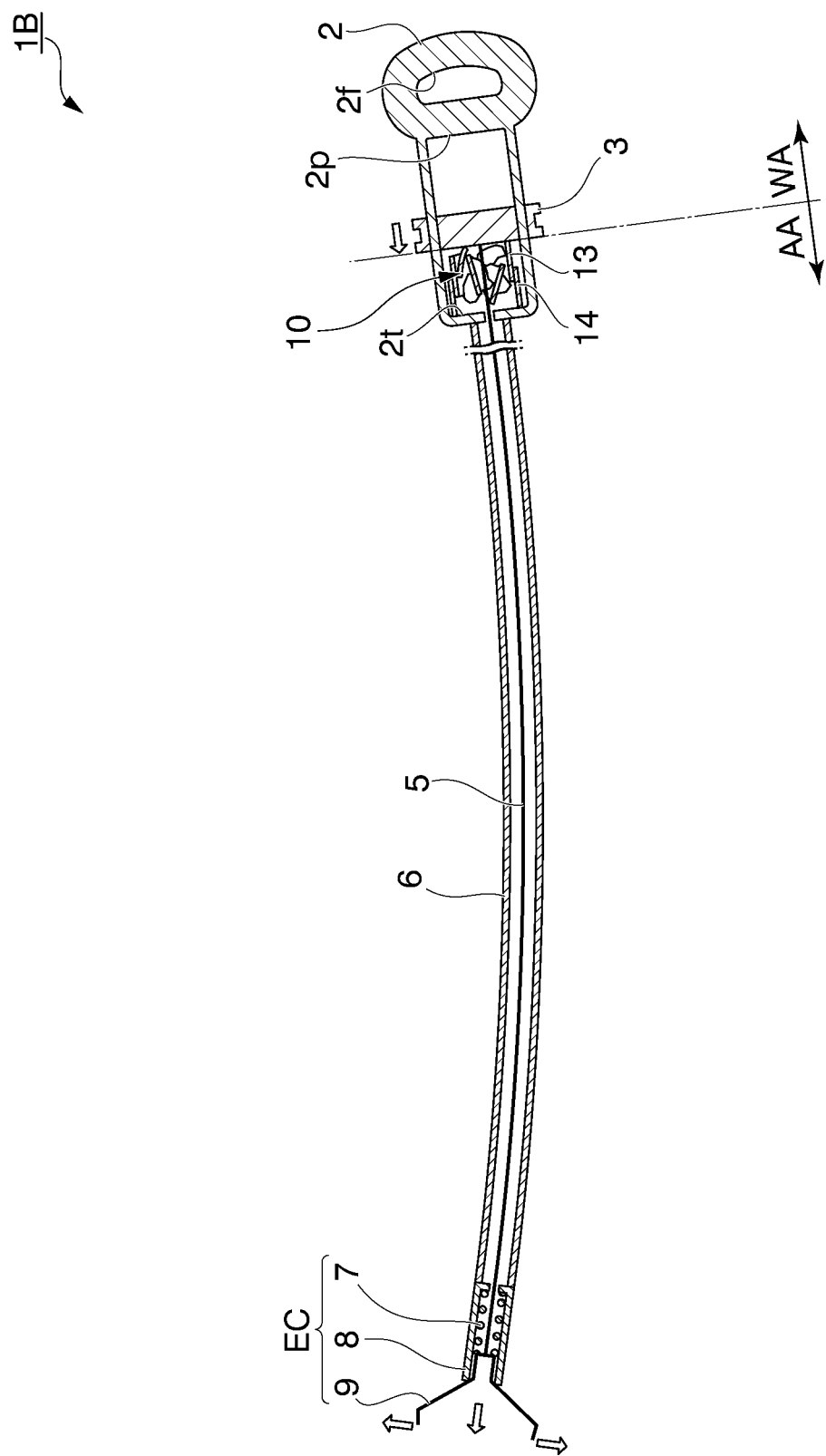
FIG. 19 is a cross-sectional view showing the treatment device in FIG. 17 and showing the operational range when the sheath is in a bent state.

As shown in FIG. 19, the treatment device 1B is configured that the sheath 6 substantially extends to be longer when the sheath 6 is in the bending state, the compression force F2 applies to the coil 12 so as to cause the coil 12 to yield at the stroke amount that the arm member 9 is at the second position. Since the coil 12 yields to the compression force F2, the dimension in the axial direction of the slider restriction mechanism 10 reduces. The slider restriction mechanism 10 is contracted such that the operation range of the slider 3 becomes to the standby range WA and the operational range AA (second state).

Figure 20:
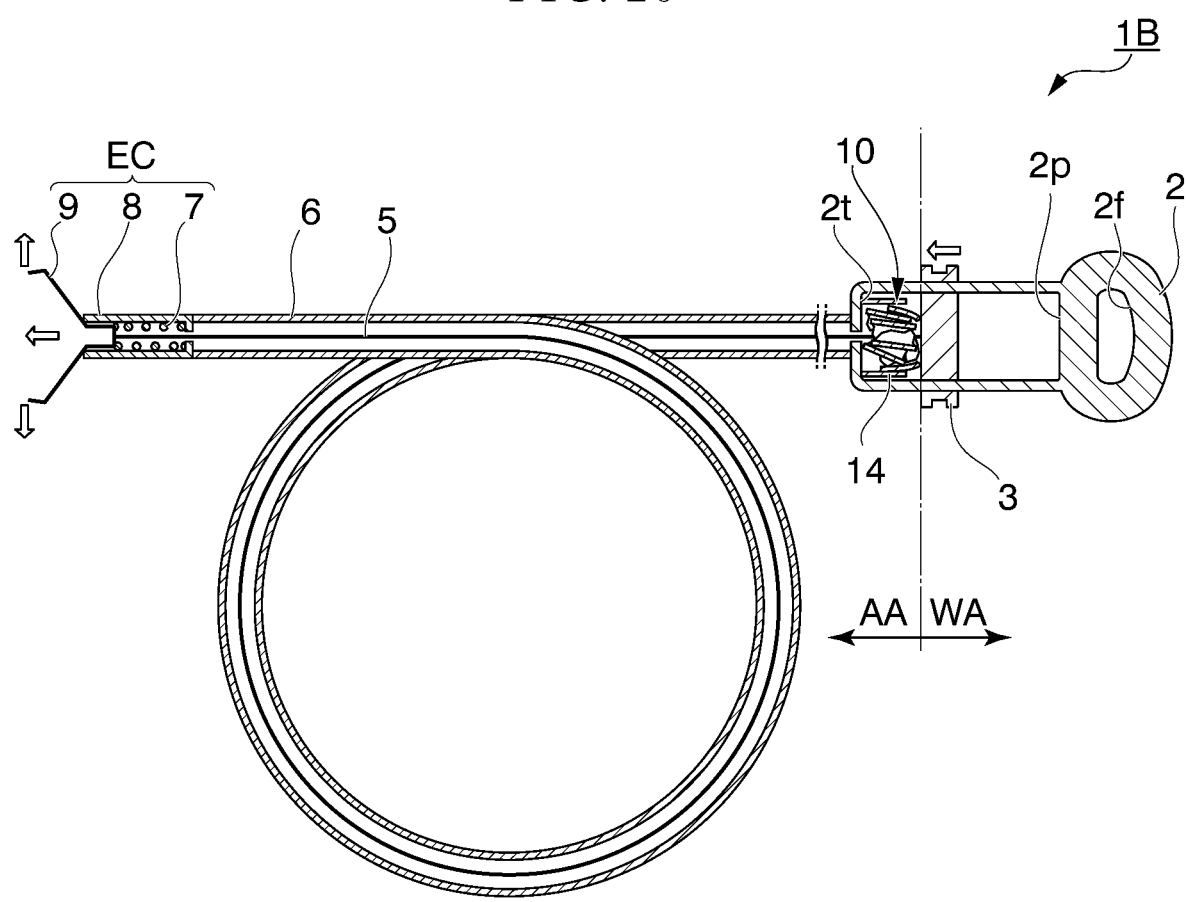
FIG. 20 is a cross-sectional view showing the treatment device in FIG. 17 and showing the operational range when the sheath is in a once-wrapped state.

As shown in FIG. 20, the treatment device 1B is configured that the sheath 6 substantially extends to be longer when the sheath 6 is in the once-wrapped state, the compression force F3 applies to the coil 13 so as to cause the coil 13 to yield at the stroke amount that the arm member 9 is at the second position. Since the coil 13 yields to the compression force F3, the dimension in the axial direction of the slider restriction mechanism 10 reduces. The slider restriction mechanism 10 is contracted such that the operation range of the slider 3 becomes the standby range WA and the operational range AA (second state).

According to the treatment device 1B according to the present embodiment, despite of the bending state of the sheath 6, the bias toward the distal end side applied to the arm member 9 in the standby range WA is suppressed by the slider restriction mechanism 10 via the wire 5 and the slider 3. Accordingly, despite of the bending state of the sheath 6, at the time of making the treatment device 1A reach the treatment target site while accommodating the arm member 9 in the pipe 8, it is not necessary for the user to pull the slider 3.

Furthermore, the slider restriction mechanism 10 has the resistance force against the advancement of the slider 3 such that even if the user does not pull the slider 3, the arm member 9 will not project out suddenly. For example, the arm member will not project out to damage the mucous membrane at the treatment target site.

The exemplary embodiments have been described above with reference to the drawings, but the technical scope of the present disclosure is not limited to the embodiments and may include various modifications without departing from the scope of the disclosure. The configuration elements shown in the above-described embodiments and the following modifications can be properly combined.

For example, the treatment device 1 and the treatment device 1A may be configured to have the grasping portion 41 and the slider 3 to be integrally configured, or have the grasped portion 42 and the operation portion 2 to be integrally configured.

The treatment device 1 and the treatment device 1A may be configured to have the grasping portion 41 at the distal end side and the grasped portion 42 at the proximal end side.

With regard to the treatment device 1, the treatment device 1A, and the treatment device 1B, the arm member 9 may be configured as a pair of forceps such as the biopsy forceps or the grasping forceps.

With regard to the slider restriction mechanism 10 of the treatment device 1B, the slider restriction mechanism may be configured as a plurality of springs having different yield points and being provided continuously along the sliding direction of the slider rather than the spiral spring.

With regard to the slider restriction mechanism 4 of the treatment device 1, the slider restriction mechanism 4A of the treatment device 1A, and the slider restriction mechanism 10 of the treatment device 1B, they may attached to the treatment device 1, the treatment device 1A, and the treatment device 1B respectively in advance, and they may configured to be attachable thereto at the time of being used by the user.

The endoscopic clip EC included in the treatment device 1, the treatment device 1A, and the treatment device 1B may be configured to exclude the elastic member 7. The arm member 9 is biased in the open state, and the distal end of the arm member 9 is exposed from the pipe 8 such that the arm member 9 comes in contact with the distal end of the pipe 8. Accordingly, the arm member 9 applies the force toward the proximal end side to the distal end of the pipe 8, and the reaction force makes the arm member 9 to be biased toward the distal end side such that the arm member 9 can be biased toward the distal end side without providing the elastic member 7.

What is claimed is:

1. A treatment device, comprising:
   an arm member including a plurality of arms and configured to operate in an open state and a closed state;
   a wire configured to attach to and detach from the arm member;
   a sheath through which the wire is inserted;
   an operator connected to a proximal end of the sheath;
   a slider connected to the wire and attached to the operator, the slider being configured to slide between a distal end or a proximal end of the operator, the slider being in a first range when the slider is disposed on the proximal end and the slider being in a second range when the slider is disposed on the distal end; and
   a slider restriction mechanism provided between the distal end of the operator and the slider, wherein:
   when the slider is disposed in the first range, the slider restriction mechanism is configured to restrict an operational range of the slider in the first range,
   when a user applies a force to move the slider from the first range to the second range, the slider restriction mechanism is configured to move from a first state in which the slider is restricted to movement in the first range to a second state in which the slider can operate in both the first range and the second range,
   the slider restriction mechanism includes a ratchet structure including a first member and a second member,
   when the slider restriction mechanism is moved from the first state to the second state, the first member is configured to move along a sliding direction of the slider so as to pass by the second member, and
   when the slider restriction mechanism is in the second state, the first member and the second member are configured to be unable to separate from each other.

2. The treatment device according to claim 1, further comprising a pipe provided at a distal end of the sheath, wherein:
   the wire is configured to be inserted through the sheath, and the pipe is configured to accommodate the arm member;
   the arm member is configured to operate in a first position and a second position, at least part of the arm member is accommodated in the pipe at the first position, and the arm member is ejected from the distal end of the pipe at the second position, and
   the arm member is biased when moving from the first position to the second position.

3. The treatment device according to claim 2, wherein when the slider restriction mechanism is in the second state and the arm member is at the second position, the arm member is moved to the first position by moving the slider to the first range despite a bending state of the sheath.

4. The treatment device according to claim 2,
   wherein the first member is only configured to pass by the second member along the sliding direction when the first member and the second member are engaged with each other.

5. The treatment device according to claim 3,
   wherein the slider restriction mechanism further comprises a spring having a resistance force against an advancement of the slider,
   in the first state, when a bending degree of the sheath increases, the sheath extends and the slider moves to a distal end side of the operator, while the slider restriction mechanism is reversibly contracted, and
   in the second state, a force from the distal end of the operator and the slider is applied to the slider restriction mechanism such that the slider restriction mechanism is irreversibly contracted.

6. The treatment device according to claim 5, wherein when the first member is engaged with the second member, the first member is configured to move in a first direction and is configured to not move in a second direction, the first direction being opposite the second direction along the sliding direction of the slider;
   the first member is not engaged with the second member in the first state, and
   the first member is engaged with the second member in the second state.

7. The treatment device according to claim 2, further comprising an elastic member provided at the pipe, wherein the elastic member has a force to bias the arm member to the second position.

8. The treatment device according to claim 2, wherein the arm member is a pair of forceps.

9. The treatment device according to claim 1, wherein the slider is configured to move the plurality of arms into the closed state when the slider is disposed in the first range, and the slider is configured to move the plurality of arms into the open state when the slider is disposed in the second range.

10. The treatment device according to claim 1, wherein:
the first member includes a first protrusion;
the second member includes a second protrusion;
when the slider restriction mechanism is moved from the first state to the second state, the first member is configured to pass by the second member along the sliding direction of the slider such that the first protrusion and the second protrusion pass over each other, and
in the second state, the first protrusion and the second protrusion engage each other such that movement of the slider restriction mechanism back to the first state from the second state is prevented.

* * * * *